US011596567B2

(12) United States Patent
Ushpizin et al.

(10) Patent No.: US 11,596,567 B2
(45) Date of Patent: Mar. 7, 2023

(54) SYSTEMS AND METHODS FOR DETERMINING AND MAINTAINING A CENTER OF ROTATION

(71) Applicant: MAZOR ROBOTICS LTD., Caesarea (IL)

(72) Inventors: Yonatan Ushpizin, Glil Yam (IL); Arik Levy, Herzliya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 345 days.

(21) Appl. No.: 17/063,299

(22) Filed: Oct. 5, 2020

(65) Prior Publication Data
US 2022/0104986 A1 Apr. 7, 2022

(51) Int. Cl.
| | | |
|---|---|---|
| A61G 13/02 | (2006.01) | |
| A61G 13/10 | (2006.01) | |
| A61B 34/20 | (2016.01) | |
| A61B 34/37 | (2016.01) | |
| A61G 99/00 | (2006.01) | |

(52) U.S. Cl.
CPC ............ *A61G 13/104* (2013.01); *A61B 34/20* (2016.02); *A61B 34/37* (2016.02); *A61G 13/02* (2013.01); *A61G 99/00* (2013.01); *A61G 2203/10* (2013.01); *A61G 2203/30* (2013.01)

(58) Field of Classification Search
CPC ...... A61G 13/104; A61G 13/02; A61G 99/00; A61B 34/20; A61B 34/37
See application file for complete search history.

(56) References Cited

U.S. PATENT DOCUMENTS

| | | | |
|---|---|---|---|
| 6,684,129 B2 | 1/2004 | Salisbury, Jr. et al. | |
| 8,655,429 B2 | 2/2014 | Kuduvalli et al. | |
| 9,827,054 B2 | 11/2017 | Richmond et al. | |
| 10,555,777 B2* | 2/2020 | Griffiths | A61G 13/06 |
| 10,667,876 B2 | 6/2020 | Maillet et al. | |
| 2012/0101508 A1 | 4/2012 | Wook Choi et al. | |
| 2014/0249546 A1 | 9/2014 | Shvartsberg et al. | |
| 2017/0196643 A1* | 7/2017 | Popovic | A61B 34/30 |
| 2018/0177469 A1 | 6/2018 | Suga | |

(Continued)

FOREIGN PATENT DOCUMENTS

| | | |
|---|---|---|
| CN | 102697559 | 3/2016 |
| WO | WO 2016/069655 | 5/2016 |
| WO | WO 2020/079596 | 4/2020 |

OTHER PUBLICATIONS

International Search Report and Written Opinion for International (PCT) Patent Application No. PCT/IL2021/051050, dated Nov. 30, 2021, 12 pages.

(Continued)

*Primary Examiner* — Fredrick C Conley
(74) *Attorney, Agent, or Firm* — Sheridan Ross P.C.

(57) ABSTRACT

Methods and systems for determining and maintaining a center of rotation are provided. A center of rotation may be determined based on first information about a robotic region of interest of a robot and second information about a patient region of interest. An operating table having multiple degrees of freedom may be caused to rotate about the center of rotation from a first position to a second position. A control system may be caused to control the robot based on the operating table being in the second position.

20 Claims, 4 Drawing Sheets

(56) References Cited

U.S. PATENT DOCUMENTS

| | | |
|---|---|---|
| 2019/0069963 A1 | 3/2019 | Azizian et al. |
| 2019/0142533 A1 | 5/2019 | Itkowitz et al. |
| 2019/0269468 A1 | 9/2019 | Hsu et al. |
| 2019/0293935 A1 | 9/2019 | Schneider et al. |
| 2020/0022775 A1 | 1/2020 | Garcia Kilroy et al. |
| 2020/0069377 A1 | 3/2020 | Finley et al. |

OTHER PUBLICATIONS

"Effectiveness of Robotics and Computer Assisted Navigation in Surgery for Knee and Hip Replacements," All Answers Ltd., Nov. 2018, 9 pages [retrieved online from: ukdiss.com/examples/robotics-surgery-knee-replacement-effectiveness.php#citethis].

Faraz "Mechanisms and Robotic Extenders for Laparoscopic Surgery," Simon Fraser University, Oct. 1998, Thesis submitted in partial fulfillment of the requirements for the degree of Doctor of Philosophy in the School of Engineering Science, 210 pages.

Huang et al. "An EOG-based wheelchair robotic arm system for assisting patients with severe spinal cord injuries," Journal of Neural Engineering, Feb. 2019, vol. 16, No. 2, Article 026021, 10 pages.

Miroir et al. "Mechanical Design and Optimization of a Microsurgical Robot," Proceedings of EUCOMES 08, 2009, M. Ceccarelli (ed.), Springer, Dordrecht, pp. 575-583.

\* cited by examiner

SYSTEMS AND METHODS FOR DETERMINING AND MAINTAINING A CENTER OF ROTATION

FIELD

The present technology is related generally to controlling an operating table, and more particularly, to determining and maintaining a center of rotation for the operating table.

BACKGROUND

An operating table can have multiple degrees of freedom and can rotate and/or translate to position a patient at a desired location. Robots may be used in connection with some surgeries, whether to assist a surgeon and/or to complete a surgical procedure autonomously.

SUMMARY

Example aspects of the present disclosure include:

An operating table control system according to at least one embodiment of the present disclosure comprises a memory storing instructions; and a processor configured to execute the instructions, the instructions causing the processor to: determine, based on first information about a robotic region of interest of a robot and second information about a patient region of interest, a center of rotation, cause an operating table having multiple degrees of freedom to rotate about the center of rotation from a first position to a second position, and control the robot based on the operating table being in the second position.

Any of the aspects herein, wherein the second information comprises a preoperative plan.

Any of the aspects herein, wherein the second position corresponds to a step of the preoperative plan.

Any of the aspects herein, wherein the operating table is movable independent of the robot.

Any of the aspects herein, wherein the instructions further cause the processor to automatically update a registration between a robotic coordinate space and a patient coordinate space based on the rotation of the operating table from the first position to the second position.

Any of the aspects herein, wherein the patient region of interest is a volume greater than a volume of the robotic region of interest, and the operating table is selectively movable to bring any location in the patient region of interest within the robotic region of interest.

Any of the aspects herein, wherein the center of rotation is a first center of rotation and wherein the instructions further cause the processor to determine a second center of rotation based on the robotic region of interest and the patient region of interest.

Any of the aspects herein, wherein the robotic region of interest includes a plurality of robotic regions of interest, each corresponding to one of a plurality of robots.

Any of the aspects herein, wherein the instructions further cause the processor to determine a combined robotic region of interest based on the plurality of robotic region of interests.

Any of the aspects herein, wherein the center of rotation is further based on the combined robotic region of interest.

Any of the aspects herein, wherein the second information corresponds to at least one of input from a surgeon, sensor data from at least one sensor, or input from a navigation system.

Any of the aspects herein, wherein the patient region of interest is positioned above a surface of the operating table.

Any of the aspects herein, wherein the patient region of interest is smaller than the robotic region of interest, and rotation of the operating table about the center of rotation ensures that the patient region of interest remains within the robotic region of interest.

A method for determining and maintaining a center of rotation according to at least one embodiment of the present disclosure comprises determining, based on first information about a robotic region of interest of a robot and second information about a patient region of interest, a center of rotation; causing an operating table having multiple degrees of freedom to rotate about the center of rotation from a first position to a second position; and causing a control system to control the robot based on the operating table being in the second position.

Any of the aspects herein, wherein the second information comprises a preoperative plan.

Any of the aspects herein, wherein the second position corresponds to a step of the preoperative plan.

Any of the aspects herein, wherein the operating table is movable independent of the robot.

Any of the aspects herein, wherein the second information corresponds to at least one of input from a surgeon, sensor data from at least one sensor, or input from a navigation system.

A method determining and maintaining a plurality of centers of rotation according to at least one embodiment of the present disclosure comprises determining a first center of rotation based on first information about a robotic region of interest and second information about a first patient region of interest; determining a second center of rotation based on the first information and third information about a second patient region of interest; causing an operating table having multiple degrees of freedom to rotate about the first center of rotation from a first position to a second position; causing a control system to control the robot based on the operating table being in the second position; causing the operating table to move to a third position to position the second center of rotation within the robotic region of interest; and causing the control system to control the robot based on the operating table being in the third position.

Any of the aspects herein, wherein the first center of rotation corresponds to a first surgical procedure in the first patient region of interest and the second center of rotation corresponds to a second surgical procedure in the second patient region of interest.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
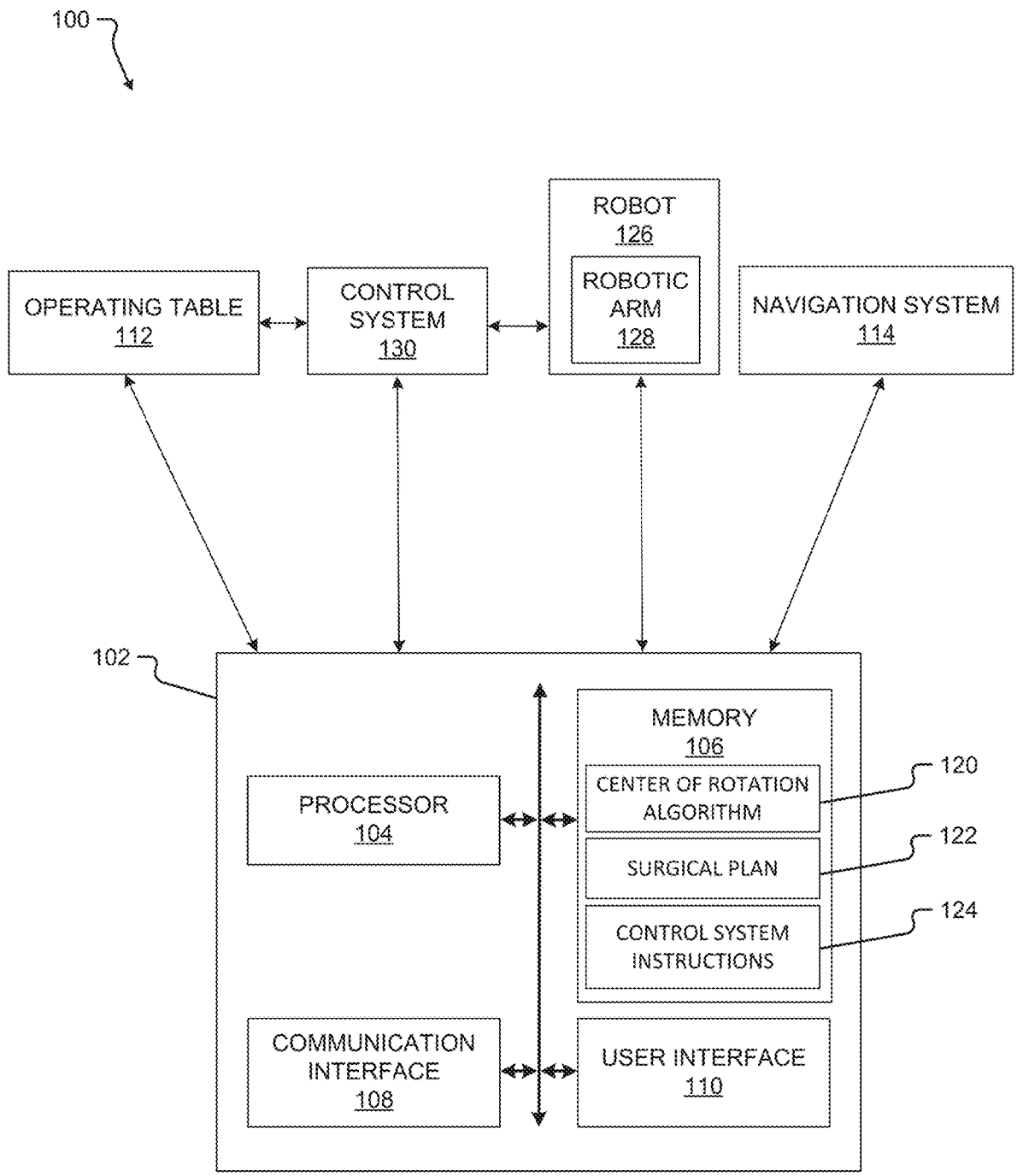
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

When a surgical robot is used in connection with an operating table, movement of the table allows an area of interest where a surgical procedure is being performed to remain within reach of the surgical robot. Movement of the table may enable movement of the patient without compromising the surgical robot's reach of the area of interest. Such movements may occur at the beginning of the procedure or during the procedure.

During surgery on a patient (e.g., a spine surgery), the patient's position may need to be modified. Where the surgery is a robotic surgery with an operating table and a robot that are independently movable, the patient position may need to be adjusted to keep the region of interest of the patient within a robot work volume. A table with at least two positioning degrees of freedom and one rotational degrees of freedom may enable a surgeon to rotate a patient (e.g., by rotating the operating table) around any center of rotation to keep the region of interest within the robot work volume.

Embodiments of the present disclosure comprise or utilize a control system for determining a center of rotation of a table to maintain a patient region of interest ("ROI") within a robotic region of interest. The control system enables a table and a robot to move independently of each other and/or enables the patient to be moved while maintaining the patient ROI within the robotic ROI. The present disclosure enables efficient use of robots that are detached from and independent of an operating table. Thus, surgical procedures utilizing robots independent of an operating table may be streamlined by maintaining a positioning of a patient within a robot's work volume without needing to reposition or move the robot for a particular patient region of interest. Additionally, the present disclosure enables efficient use of larger robots that cannot be moved as easily as an operating table.

As described more fully below, methods and systems for maintaining a patient region of interest within a robotic region of interest according to at least some embodiments of the present disclosure may beneficially comprise determining a center of rotation for an operating table to rotate or otherwise move about, and causing a control system to control the robot based on the operating table rotating about the center of rotation.

Turning first to FIG. 1, a block diagram of a system 100 according to at least one embodiment of the present disclosure is shown. The system 100 may be used to execute a center of rotation algorithm 120 and/or carry out other aspects of one or more of the methods disclosed herein. The system 100 comprises a computing device 102, an operating table 112, a navigation system 114, one or more robots 126, and/or one or more control systems 130. Systems according to other embodiments of the present disclosure may comprise more or fewer components than the system 100. For example, the system 100 may not include the navigation system 114.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the operating table 112, the control system 130, the robot 126, and/or the navigation system 114. The instructions may also cause the processor 104 to carry out, and/or to generate one or more commands or signals that cause one or more other components of the system 100 to carry out, one or more steps of any method described herein.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 or 400 described herein. The memory 106 may store, for example, one or more center of rotation algorithms 120, one or more control system instructions 124, and/or one or more surgical plans 122. the algorithms 120 and/or control system instructions 124 may, in some embodiments, be organized into one or more applications, modules, packages, layers, or engines. The algorithms may cause the processor 104 to manipulate data stored in the memory 106, reflected in a surgical plan 122, and/or received from the operating table 112, the robot 126, the control system 130, and/or the navigation system 114.

The computing device 102 may also comprise a communication interface 108. The communication interface 108 may be used for receiving information from an external source (such as the operating table 112 (e.g., from one or more sensors or other smart elements of the operating table 112), the navigation system 114, the control system 130, and/or the robot 126), and/or for transmitting instructions, images, and/or other information to an external system or device (e.g., another computing device 102, the navigation system 114, the operating table 112, the control system 130, and/or the robot 126). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding determining a first center of rotation; to receive a user selection or other user input regarding determining a second center of rotation; to receive a user selection or other user input regarding causing an operating table 112 to rotate about the first center of rotation from a first position to a second position; to receive a user selection or other user input regarding causing a control system 130 to control a robot 126 based on the operating table 112 being in the second position; to receive a user selection or other user input regarding causing the operating table 112 to move to a third position to position the second center of rotation within a robotic region of interest; to receive a user selection or other user input regarding causing the control system 130 to control the robot 126 based on the operating table 112 being in the third position; and/or to display the image data and/or the surgical plan 122. In some embodiments, the user interface 110 may be useful to allow a surgeon or other user to modify the plan 122, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

Turning to the operating or surgical table 112, the table 112 is operable to maneuver a patient while maintaining a specific anatomy of the patient within a region of interest of the robot 126. In some embodiments, the table 112 has two positioning degrees of freedom and one rotational degrees of freedom, which allows positioning of the specific anatomy of the patient anywhere in space (within a volume defined by the limits of movement of the table 112). For example, the table 112 can slide forward and backward and from side to side, and can tilt (e.g., around an axis positioned between the head and foot of the table 112, and extending from one side of the table 112 to the other) and/or roll (e.g., around an axis positioned between the two sides of the table 112, and extending from the head of the table 112 to the foot thereof). In other embodiments, the table 112 can bend at one or more areas (which bending may be possible due to, for example, the use of a flexible surface for the table 112, or by physically separating one portion of the table 112 from another portion of the table 112 and moving the two portions independently). The table 112 may be manually moved or manipulated by, for example, a surgeon or other user, or the table 112 may comprise one or more motors, actuators, and/or other mechanisms configured to enable movement and/or manipulation of the table 112 by the control system 130. The robot 126 may be independent of and unattached to the table 112 in some embodiments. In other words, the robot 126 may be manipulated and moved separately from the table 112. In such embodiments, the robot 126 may be secured to one or more of a floor, wall, and/or ceiling of an operating room, or to any structure affixed to any of the foregoing. In other embodiments, the robot 126 may be attached to the table 112.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room where a surgery takes place. In various embodiments, the navigation system 114 may be used to track a position of a patient (or, more particularly, of a navigated reference marker attached, directly or indirectly, in fixed relation to the patient), the operating table 112 (or, more particularly, of a navigated reference marker attached, directly or indirectly, in fixed relation to the table 112), and/or of the robot 126 (or, more particularly, of a navigated reference marker attached, directly or indirectly, in fixed relation to the robot 126). The navigation system 114 may include a display for displaying one or more images from an external source (e.g., the computing device 102 or other source) or a video stream from the camera or other sensor of the navigation system 114.

In some embodiments, the navigation system 114 may be used to track movement of the robot 126, the table 112, and/or the patient and may provide feedback regarding, or confirmation of, a position of the robot 126, the table 112, and/or the patient. For example, the navigation system 114 may indicate—audibly and/or visually via a display—that the robot 126 and/or the table 112 needs to be moved, automatically or manually, to a suggested robot or table position based on a center of rotation, the patient region of interest, and/or the robotic region of interest. The navigation system 114 can monitor or track the robot 126 or the table 112 as the robot 126 or the table 112 is moved toward the suggested robot or table position, or to any other position. The navigation system 114 can further indicate to or alert a user when the robot 126 or the table 112 has reached the suggested robot position or any other predetermined position. In other embodiments, a user may view a display of the navigation system 114 while moving the robot 126 or the table 112 to the suggested robot or table position, so as to ensure that the user moves the robot 126 or the table 112 to the correct position. In some embodiments, the system 100 can operate without the use of navigation system 114.

Reference markers (i.e., navigation markers) may be placed on the robot 126, a robotic arm 128 of the robot 126, the table 112, a patient, and/or any other object in the surgical space. The reference markers may be tracked by the navigation system 114, and the results of the tracking may be used by the robot 126 and/or by an operator of the system 100 or any component thereof. As described above, in some embodiments, the navigation system 114 can be used to track other components of the system 100 (e.g., operating table 112).

The robot 126 may be any surgical robot or surgical robotic system. The robot 126 may be or comprise, for example, the Mazor X™ Stealth Edition robotic guidance system. The robot 126 may comprise the robotic arm 128. In some embodiments, the robotic arm 128 may comprise a plurality of robotic arms, though the robot 126 may comprise one robotic arm, two robotic arms, or more than two robotic arms. The robotic arm 128 may be used to selectively hold and/or operate one or more surgical tools, an imaging device, one or more reference markers, and/or any other tool or instrument.

In the illustrated embodiment, the system 100 includes the control system 130, though in some embodiments the system 100 may not include the control system 130. In other embodiments, the control system 130 may be integrated into the computing device 102, the robot 126, and/or the operating table 112. The control system 130 may include a controller that may be an electronic, a mechanical, or an electro-mechanical controller. The control system 130 may comprise or may be any processor described herein. The control system 130 may comprise a memory storing instructions for executing any of the functions or methods described herein as being carried out by the control system 130. In some embodiments, the control system 130 may be configured to simply convert signals received from the computing device 102 (e.g., via a communication interface 108) into commands for operating the operating table 112, the navigation system 114, and/or the robot 126. In other embodiments, the control system 130 may be configured to process and/or convert signals received from the operating table 112, the navigation system 114, and/or the robot 126. Further, the control system 130 may receive signals from one or more sources (e.g., the operating table 112, the navigation system 114, and/or the robot 126) and may output signals to one or more sources. In some embodiments, the functions of the control system as described herein may be performed by the computing device 102, and the system 100 may not comprise a separate control system 130.

Figure 2A:
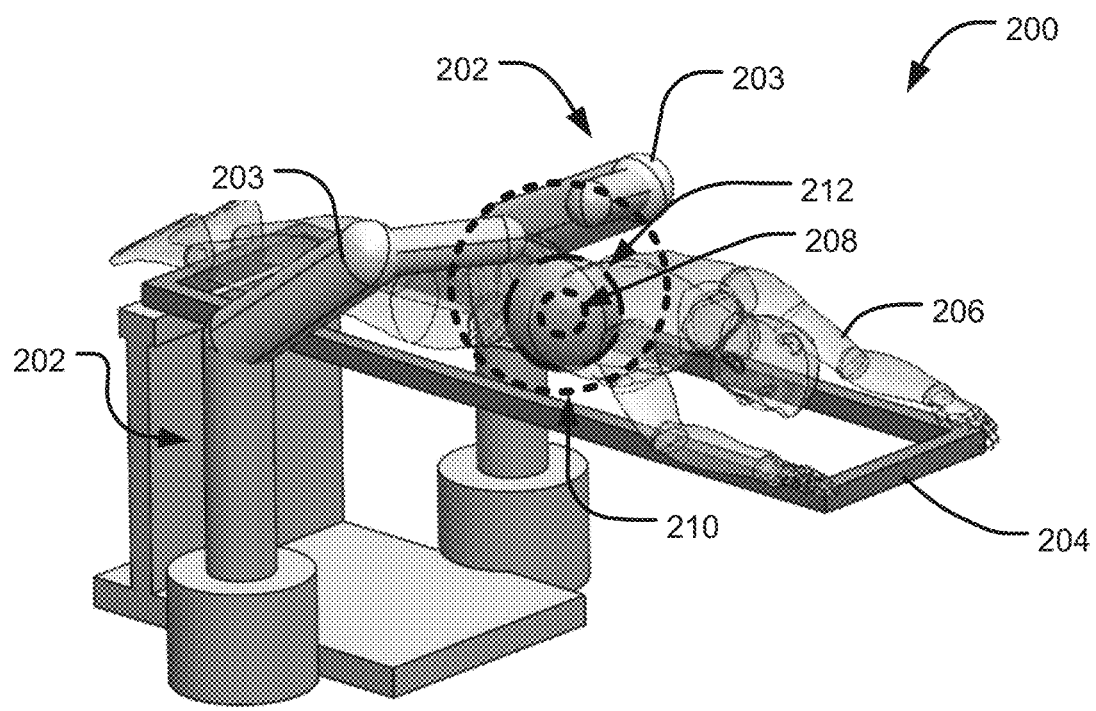
FIG. 2A is an image of an operating table and a robot.
Figure 2B:
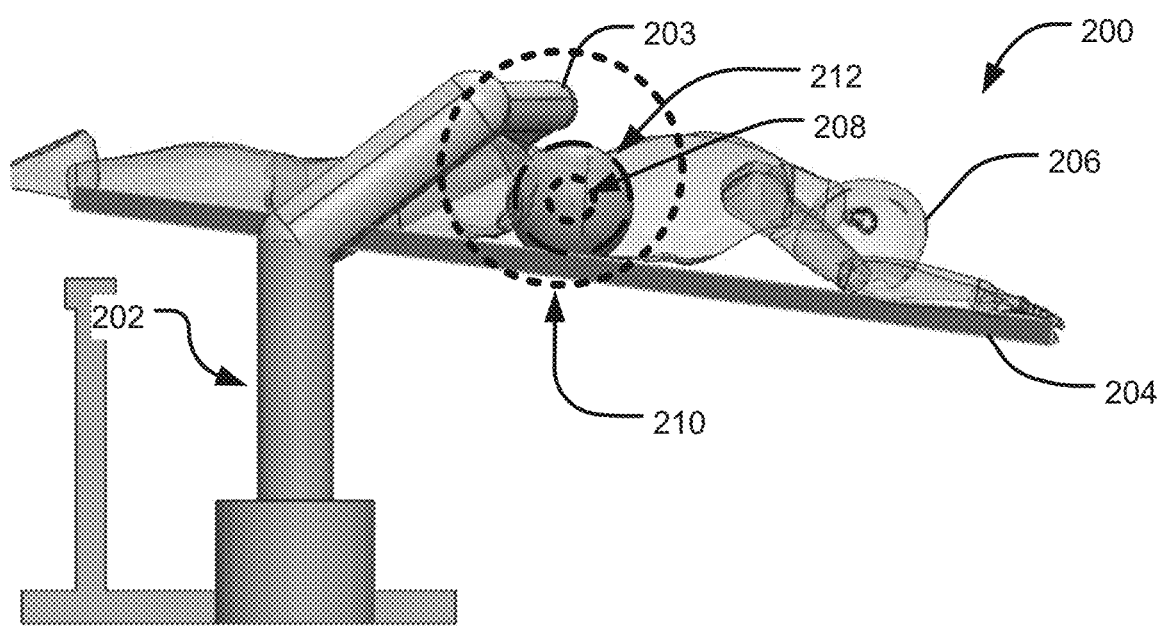
FIG. 2B is another image of the operating table and the robot.

Turning to FIGS. 2A and 2B, at least a portion of a surgical room 200 is illustrated including two robots 202 (each of which may be the same as or similar to the robot 126 described above) each having a robotic arm 203 (which may be the same as or similar to the robotic arm 128), an operating table 204 (which may be the same as or similar to the table 112 described above), and a patient 206 laying prone on the table 204. The table 204 is movable from a first position, as shown in FIG. 2A, to a second position, as shown in FIG. 2B. In the illustrated example, the movement of the table 204 from the first position shown in FIG. 2A to the second position shown in FIG. 2B is a tilting movement, though the table 204 may move in any direction or orientation. The table 204 may be moved as needed during a procedure and/or may be moved based on and/or in preparation for one or more steps of a surgical or preoperative plan 122. As previously described, the table 204 may be moved manually by a surgeon or operator or may be moved automatically by the control system 130 and one or more motors, actuators, and/or other mechanisms.

The table 204 selectively moves about a center of rotation (COR) 208, depicted as a first dashed sphere, which may be determined, for example, from first information and second information. The first information may correspond to information about a robotic region of interest (ROI) 210, depicted as a second dashed sphere, and the second information may correspond to information about a patient region of interest (ROI) 212, depicted as a third dashed sphere. It will be understood that the COR, patient ROI, and/or robotic ROI may be any shape or size. Further, the first dashed sphere, the second dashed sphere, and the third dashed sphere are demonstrative and are not visible in practice though it will also be appreciated that such COR, patient ROI, and/or robotic ROI may be displayed in an augmented or virtual reality headset or other display (e.g., a monitor).

The robotic ROI 210 correlates to a dimensional reach of the robotic arm 203. In some embodiments, the robotic ROI 210 may be or comprise a plurality of robotic ROIs and each robotic ROI may correspond to one of a plurality of robotic arms. In other words, in embodiments where a plurality of robotic arms is used during a procedure, each robotic arm will have its own robotic ROI. The robotic ROIs of each of a plurality of robots may overlap in whole or in part. In such embodiments having a plurality of robotic ROIs, a combined robotic ROI (e.g., an ROI the entirety of which may be reached by each of the plurality of robots) may be calculated or determined and the combined robotic ROI may be used to determine the COR 208.

The patient ROI 212 correlates to an area of and/or surrounding a surgical site that the robot 202 (or a surgeon) may contact, access, or within which the robot 202 (or surgeon) may otherwise move. The patient ROI 212 can be positioned above a surface of the table 204. The patient ROI 212 may have a volume greater than, less than, or equal to a volume of the robotic ROI 210. Similarly, the patient ROI 212 may have the same shape or a different shape than a shape of the robotic ROI 210. In embodiments where the patient ROI 212 is smaller than the robotic ROI 210, rotation of the table 112 about the COR 208 ensures that the patient ROI 212 remains within the robotic ROI 210. In embodiments where the patient ROI 212 is greater than the robotic ROI 210, the operating table may be selectively moved to bring any location in the patient ROI 212 within the robotic ROI 210.

In some embodiments, more than one COR 208 may be calculated. For example, in embodiments where the patient ROI 212 is greater than the robotic ROI 210 and the robotic arm 203 cannot reach all areas of the patient ROI 212, first and second CORs 208 may be determined. In other examples, a first COR 208 may correspond to a first surgical procedure in a first area of the patient 206 and a second COR 208 may correspond to a second surgical procedure in a second area of the patient 206. In such embodiments, the table 204 may selectively move from the first position to the second position about the first COR 208. The table 204 may then move to position the second COR 208 within the robotic ROI 210. Alternatively, the robot 202 may move to position the robotic ROI 210 such that the second COR 208 is within the robotic ROI 210. When the robotic ROI 210 and the second COR 208 are aligned or otherwise positioned, the table 204 may rotate about the second COR 208 to maintain the patient ROI 212 within the robotic ROI 210.

Figure 3:
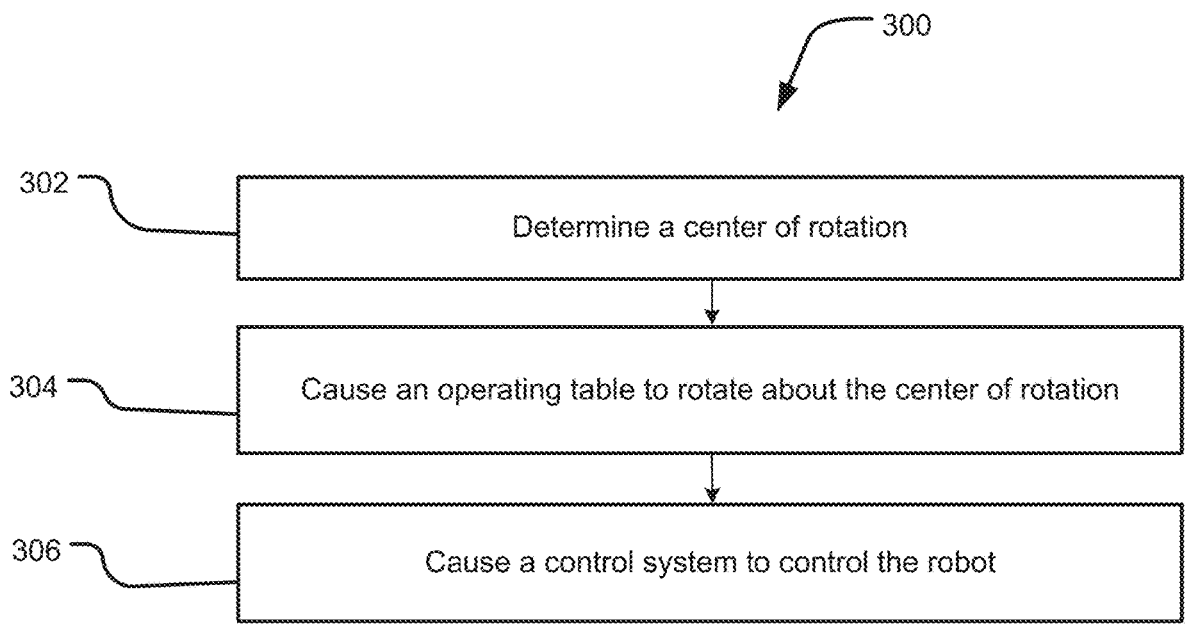
FIG. 3 is a flowchart of a method according to at least one embodiment of the present disclosure.

Turning now to FIG. 3, a method 300 for determining and maintaining a center of rotation may be executed in whole or in part, for example, on a computing device such as the computing device 102 or similar device, and may utilize one or more other components of the system 100 or similar components. One or more aspects of the method 300 may be performed by or with a surgical robot, a surgeon, or a combination of both.

The method 300 comprises determining, based on first information and second information, a center of rotation such as the center of rotation (COR) 208 (step 302). The COR may be determined using a center of rotation algorithm such as the center of rotation algorithm 120, and the algorithm may receive the first information and the second information as inputs.

The first information may correspond to a robotic region of interest (ROI) such as the robotic ROI 210 of a robot such as the robot 126 or 202. The second information may correspond to a patient ROI such as the patient ROI 212. The first information and/or the second information may be received via a user interface such as the user interface 110 and/or via a communication interface such as the communication interface 108 of a computing device such as the computing device 102, and may be stored in a memory such as the memory 106. The first information and/or the second information may also be generated by and/or uploaded to any other component of the system. In some embodiments, the first information may be received directly from the robot. The first information may include a dimensional reach of a robotic arm such as the robotic arm 128 or 203, dimensions of the robot and/or of the robotic arm, degrees of freedom of the robotic arm, and/or whether the robot is independent of an operating table such as the table 112 or 204.

In various embodiments, the second information (pertaining to the patient ROI) corresponds to at least one of input from a surgeon, sensor data from at least one sensor, or input from a navigation system such as the navigation system 114. In other embodiments, the second information may comprise or be extracted or otherwise obtained from a surgical or preoperative plan such as the surgical plan 122. In further embodiments, a marker may be placed within the desired patient ROI and tracked by a navigation system, such as the navigation system 114. In other embodiments, a marker may be placed on the desired patient ROI and imaged by an imaging device, such as an X-ray based imaging device or ultrasound device. In either case, the marker may be secured, for example, either temporarily or permanently to an anatomical element within the patient ROI. In such embodiments, the marker may be used to define (or at least to assist in defining) the patient ROI, which may then be used as at least one input to determine the COR.

The method 300 also comprises causing an operating table such as the table 112 or 204 to rotate about the COR from a first position to a second position (step 304). The table may be moveable independent of the robot. In some embodiments, a registration between a robotic coordinate space and a patient coordinate space may be updated based on rotation or other movement of the operating table from the first position to the second position.

The table may also have multiple degrees of freedom and can rotate or move in any direction. In some embodiments, the table has two positioning degrees of freedom (to allow the table to move forward and backward and side-to-side) and one rotational degrees of freedom (to allow the table to tilt and roll). In other embodiments, the table can bend at one or more locations, in any manner described herein or any other manner that allows the table to continue to support the patient. The table may be manually moved or manipulated by, for example, a surgeon or other user, or the table may be caused to be moved or manipulated by a control system, such as the control system 130.

The method 300 also comprises causing a control system (such as the control system 130, for example) to control the robot based on the operating table being in the second position (step 306). The control system may receive control system instructions such as the control system instructions 124 from a computing device such as the computing device 102. The control system instructions may cause the control system to control the robot. The control system instructions may be received via the user interface and/or via the communication interface of the computing device and may be stored in the memory. The control system instructions may also be generated by and/or uploaded to any other component of the system 100. In some embodiments, the control system instructions are based on a surgical plan such as the surgical plan 122. For example, each movement of the robot may correlate to a surgical step of the surgical plan.

In some embodiments, the step 306 may comprise causing, with a computing device (e.g., the computing device 102), the robot to move based on, for example, a surgical plan, the position of the operating table, and/or an existing registration of a coordinate system of the robot to a coordinate system of the patient and/or to a coordinate system of a navigation system.

The method 300 may comprise, in some embodiments, receiving a surgical plan, which may be the same as or similar to the surgical plan 122. The surgical plan may be received via a user interface (e.g., the user interface 110) and/or a communication interface (e.g., the communication interface 108) of a computing device such as the computing device 102, and may be stored in a memory such as the memory 106 of the computing device. The surgical plan may include information about one or more planned movements of a tool held by the robotic arm during a surgical procedure. The surgical plan may be used to generate the control system instructions, or may comprise the control system instructions. In some embodiments, the surgical plan includes a planned trajectory of one or more medical devices (e.g., medical tools, medical screws, medical plates, etc.). The information may also include a timeline or schedule of the one or more planned movements. The one or more planned movements may include one or more of timestamps, types of movement (e.g., translational and/or rotational), durations of movement, and/or positional information (e.g., starting, intermediate, and/or ending coordinates and/or orientation).

In some embodiments, the method 300 may comprise determining information about one or more needed movements of the tool during a surgical procedure outlined or otherwise described in a surgical plan. In such embodiments, the surgical plan may not include any such information about needed movements of the tool, but a processor (whether of a computing device such as the computing device 102, or of a control system such as the control system 130, or otherwise), executing instructions stored in a memory, may generate such information based on the surgical plan.

The step 304 of causing the table to rotate about the COR from a first position to a second position may be further based on the surgical plan. For example, in some embodiments, the method 300, and more specifically the step 304, may comprise causing the operating table to rotate about the COR from a first position to a second position wherein the second position corresponds to a step of the plan. In such embodiments, the plan may include information about a needed movement of the operating table (and/or of the patient) from the first position to the second position, or a determination to move the operating table (and thus the patient) from the first position to the second position may be made based on the surgical plan.

Although described herein in connection with a robot that is not connected to an operating table, the method 300 may be used in connection with robots of any kind, including robots that are connected to the table, robots that are supported on a selectively moveable cart, robots supported entirely by a patient's body, and robots that may be selectively connected to a structure other than an operating table. The present disclosure may be particularly useful, however, when the operating table and/or patient is/are movable independently of the robot.

Figure 4:
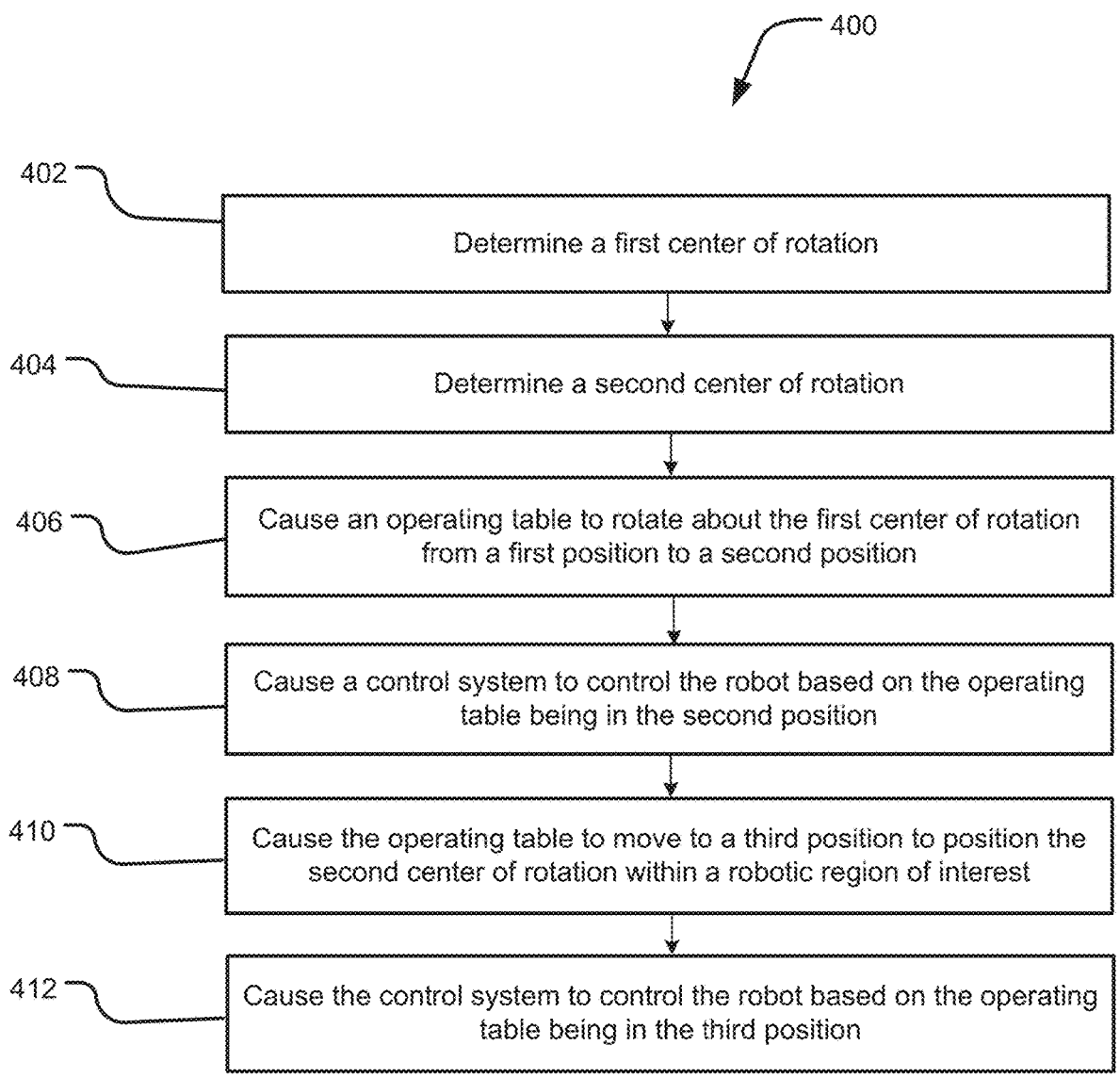
FIG. 4 is a flowchart of a method according to at least one embodiment of the present disclosure.

Turning now to FIG. 4, a method 400 for determining and maintaining a plurality of centers of rotation may be executed in whole or in part, for example, on a computing device such as the computing device 102 or similar device, and may utilize one or more other components of the system 100 or similar components. One or more aspects of the method 400 may be performed by or with a surgical robot, a surgeon, or a combination of both.

The method 400 comprises determining, based on first information and second information, a first COR of a plurality of CORs based on first information and second information (step 402) and determining a second COR of the plurality of CORs based on the first information and third information (step 404). The first COR and the second COR may each be determined using a center of rotation algorithm such as the center of rotation algorithm 120. The algorithm may receive the first information, the second information, and/or the third information as inputs. In some embodiments, the first COR may correspond to a first surgical procedure in a first patient ROI and the second COR may correspond to a second surgical procedure in a second patient ROI. For example, if a patient is to undergo a multi-level spinal surgery, the first patient ROI may correspond to a first spinal level at which a portion of the surgery will take place, and the second patient ROI may correspond to a second spinal level at which another portion of the surgery will take place. The first patient ROI and the second patient ROI may be completely separate and spaced from each other, or completely separate but with a common boundary, or may overlap. In at least some embodiments, the first and second patient ROIs are not, however, co-extensive. In other embodiments, the first and second patient ROIs (or other ROIs) may be assembled into a combined ROI and one or more CORs may be determined for the combined ROI.

The first information may correspond to a robotic ROI such as the robotic ROI 210 of a robot, such as the robot 126 or 202; the second information may correspond to the first patient ROI 212; and the third information may correspond to the second patient ROI. The first information, the second information, and/or the third information may be received via a user interface such as the user interface 110 and/or via a communication interface such as the communication interface 108 of a computing device such as the computing device 102. The first, second, and/or third information may be stored in a memory such as the memory 106. The first information, the second information, and/or the third information may also be generated by and/or uploaded to any other component of the system. In some embodiments, the first information may be received directly from the robot. The first information may include a dimensional reach of a robotic arm of the robot (which may be, for example, the same as or similar to the robotic arm 128 or 203), dimensions of the robot and/or the robotic arm, degrees of freedom of the robotic, and/or whether the robot is independent of an operating table such as the table 112 or 204.

In various embodiments, each of the second information and the third information (pertaining to the patient's first ROI and second ROI, respectively) corresponds to at least one of input from a surgeon, sensor data from at least one sensor, or input from a navigation system such as the navigation system 114. In other embodiments, the second information and/or the third information may each be extracted from or otherwise obtained from, or comprise, a surgical or preoperative plan such as the surgical plan 122. In further embodiments, a marker may be placed within the desired patient ROI and tracked by a navigation system, such as the navigation system 114. In other embodiments, a marker may be placed on the desired patient ROI and imaged by an imaging device, such as an X-ray based imaging device or ultrasound device. In either case, the marker may be secured, for example, either temporarily or permanently to an anatomical element within the patient ROI. In such embodiments, the marker may be used to define (or at least to assist in defining) the patient ROI, which may then be used as at least one input to determine the COR.

The method 400 also comprises causing an operating table such as the table 112 or 204 to rotate about the first COR from a first position to a second position (step 406). The table may be moveable independent of the robot. In some embodiments, a registration between a robotic coordinate space and a patient coordinate space (and/or between a navigation coordinate space and a patient coordinate space) may be updated based on rotation of the operating table from the first position to the second position.

The table may also have multiple degrees of freedom, which may enable the table to rotate or move in any direction. In some embodiments, the table has two positioning degrees of freedom (to allow the table to move forward and backward and side-to-side) and one rotational degrees of freedom (to allow the table to tilt and/or roll). In other embodiments, the table can bend at one or more locations (e.g., in any manner described herein). The table may be manually moved or manipulated by, for example, a surgeon or other user, or the table may be caused to be moved or manipulated by a control system, such as the control system 130.

The method 400 also comprises causing a control system (such as the control system 130, for example) to control the robot based on the operating table being in the second position (step 408). The control system may receive control system instructions such as the control system instructions 124 from a computing device such as the computing device 102. The control system instructions may cause the control system to control the robot. The control system instructions may be received via the user interface and/or via the communication interface of the computing device and may be stored in the memory. The control system instructions may also be generated by and/or uploaded to any other component of the system 100. In some embodiments, the control system instructions are based on a surgical plan such as the surgical plan 122.

In some embodiments, the step 408 may comprise causing, with a computing device (e.g., the computing device 102), the robot to move based on, for example, a surgical plan, the position of the operating table, and/or an existing registration of a coordinate system of the robot to a coordinate system of the patient and/or to a coordinate system of a navigation system.

The method 400 also comprises causing the table to move to a third position to position the second COR within the robotic ROI (step 410). The step 410 may be carried out in a substantially similar manner to the step 406. In some embodiments, the registration between a robotic coordinate space and a patient coordinate space may be updated based on movement of the table from the second position to the third position.

The method 400 also comprises causing the control system to control the robot based on the operating table being in the third position (step 412). The step 412 may be carried out in a substantially similar manner to the step 408. The control system may receive control system instructions such as the control system instructions 124 from a computing device such as the computing device 102. The control system instructions may be the same instructions as the instructions of step 408, or may be new or updated control system instructions. The control system instructions may be received via the user interface and/or via the communication interface of the computing device, and may be stored in the memory. The control system instructions may also be generated by and/or uploaded to any other component of the system. In some embodiments, the control system instructions are based on the surgical plan. For example, each movement of the robot may correlate to a surgical step of the surgical plan.

In some embodiments, the step 412 may comprise causing, with a computing device (e.g., the computing device 102), the robot to move based on, for example, a surgical plan, the position of the operating table, and/or an existing registration of a coordinate system of the robot to a coordinate system of the patient and/or to a coordinate system of a navigation system.

The method 400 may comprise, in some embodiments, receiving a surgical plan, which may be the same as or similar to the surgical plan 122. The surgical plan may be received via a user interface (e.g., the user interface 110) and/or a communication interface (e.g., the communication interface 108) of a computing device such as the computing device 102, and may be stored in a memory such as the memory 106 of the computing device. The surgical plan may include information about one or more planned movements of a tool held by the robotic arm during a surgical procedure. The surgical plan may be used to generate the control system instructions, or may comprise the control system instructions. In some embodiments, the surgical plan includes a planned trajectory of one or more medical devices (e.g., medical tools, medical screws, medical plates, etc.). The information may also include a timeline or schedule of the one or more planned movements. The one or more planned movements may include one or more of timestamps, types of movement (e.g., translational and/or rotational), durations of movement, and/or positional information (e.g., starting, intermediate, and/or ending coordinates and/or orientation).

In some embodiments, the method 400 may comprise determining information about one or more needed movements of the tool during a surgical procedure outlined or otherwise described in a surgical plan. In such embodiments, the surgical plan may not include any such information about needed movements of the tool, but a processor (whether of a computing device such as the computing device 102, or of a control system such as the control system 130, or otherwise), executing instructions stored in a memory, may generate such information based on the surgical plan.

The steps 406 and 410 of causing the table to rotate about the first COR from a first position to a second position and causing the table to move to a third position to position the second COR within the robotic ROI, respectively, may each be further based on the surgical plan. For example, in some embodiments, the method 400, and more specifically the steps 406 and 410, may comprise causing the operating table to rotate about the first COR from a first position to a second position and causing the operating table to move to a third position to position the second COR within the robotic ROI, wherein the second position and the third position each corresponds to a step of the plan. In such embodiments, the plan may include information about a needed movement of the operating table (and/or of the patient) from the first position to the second position or from the second position to the third position, or a determination to move the operating table (and thus the patient) from the first position to the second position or from the second position to the third position may be made based on the surgical plan.

Although described herein in connection with a robot that is not connected to an operating table, the method 400 may be used in connection with robots of any kind, including robots that are connected to the table, robots that are supported on a selectively moveable cart, robots supported entirely by a patient's body, and robots that may be selectively connected to a structure other than an operating table. The present disclosure may be particularly useful, however, when the operating table and/or patient is/are movable independently of the robot.

The methods and systems described herein provide a control system and method for determining a center of rotation of an operating table to align and maintain a patient region of interest within a robotic region of interest. The methods and systems described herein enables efficient use of robots that are unattached and independent of an operating table, thereby beneficially streamlining an operating procedure by maintaining a positioning of a patient within a robot's work volume without the need to reposition or move the robot.

As may be appreciated based on the foregoing disclosure, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). One or more steps of the methods described herein may be performed in an order other than the order in which they are described herein.

As may also be appreciated based on the foregoing disclosure; embodiments of the present disclosure may include one or more aspects of PCT Patent Application PCT/IB2019/058795, titled "Versatile Multi-Arm Robotic Surgical System" and filed on Oct. 15, 2020, the entirety of which is hereby incorporated by reference herein in its entirety.

The foregoing discussion has been presented for purposes of illustration and description. The foregoing is not intended to limit the disclosure to the form or forms disclosed herein.

In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An operating table control system comprising:
a memory storing instructions; and
a processor configured to execute the instructions, the instructions causing the processor to:
determine, based on first information about a robotic region of interest of a robot and second information about a patient region of interest, a center of rotation,
cause an operating table having multiple degrees of freedom to rotate about the center of rotation from a first position to a second position, and
control the robot based on the operating table being in the second position.

2. The system of claim 1, wherein the second information comprises a preoperative plan.

3. The system of claim 2, wherein the second position corresponds to a step of the preoperative plan.

4. The system of claim 1, wherein the operating table is movable independent of the robot.

5. The system of claim 1, wherein the instructions further cause the processor to automatically update a registration between a robotic coordinate space and a patient coordinate space based on the rotation of the operating table from the first position to the second position.

6. The system of claim 1, wherein the patient region of interest is a volume greater than a volume of the robotic region of interest, and the operating table is selectively movable to bring any location in the patient region of interest within the robotic region of interest.

7. The system of claim 6, wherein the center of rotation is a first center of rotation and wherein the instructions further cause the processor to determine a second center of rotation based on the robotic region of interest and the patient region of interest.

8. The system of claim 6, wherein the center of rotation is further based on the combined robotic region of interest.

9. The system of claim 1, wherein the robotic region of interest includes a plurality of robotic regions of interest, each corresponding to one of a plurality of robots.

10. The system of claim 9, wherein the instructions further cause the processor to determine a combined robotic region of interest based on the plurality of robotic region of interests.

11. The system of claim 1, wherein the second information corresponds to at least one of input from a surgeon, sensor data from at least one sensor, or input from a navigation system.

12. The system of claim 1, wherein the patient region of interest is positioned above a surface of the operating table.

13. The system of claim 1, wherein the patient region of interest is smaller than the robotic region of interest, and rotation of the operating table about the center of rotation ensures that the patient region of interest remains within the robotic region of interest.

14. A method for determining and maintaining a center of rotation comprising:
determining, based on first information about a robotic region of interest of a robot and second information about a patient region of interest, a center of rotation;
causing an operating table having multiple degrees of freedom to rotate about the center of rotation from a first position to a second position; and
causing a control system to control the robot based on the operating table being in the second position.

15. The method of claim 14, wherein the second information comprises a preoperative plan.

16. The method of claim 15, wherein the second position corresponds to a step of the preoperative plan.

17. The method of claim 14, wherein the operating table is movable independent of the robot.

18. The method of claim 14, wherein the second information corresponds to at least one of input from a surgeon, sensor data from at least one sensor, or input from a navigation system.

19. A method determining and maintaining a plurality of centers of rotation comprising:
determining a first center of rotation based on first information about a robotic region of interest and second information about a first patient region of interest;
determining a second center of rotation based on the first information and third information about a second patient region of interest;
causing an operating table having multiple degrees of freedom to rotate about the first center of rotation from a first position to a second position;
causing a control system to control the robot based on the operating table being in the second position;
causing the operating table to move to a third position to position the second center of rotation within the robotic region of interest; and
causing the control system to control the robot based on the operating table being in the third position.

20. The method of claim 19, wherein the first center of rotation corresponds to a first surgical procedure in the first patient region of interest and the second center of rotation corresponds to a second surgical procedure in the second patient region of interest.

* * * * *